US008358407B2

(12) United States Patent
Hu et al.

(10) Patent No.: US 8,358,407 B2
(45) Date of Patent: Jan. 22, 2013

(54) ENHANCING SIGNALS IN SURFACE ENHANCED RAMAN SPECTROSCOPY (SERS)

(75) Inventors: Min Hu, Sunnyvale, CA (US); Wei Wu, Palo Alto, CA (US); Fung Suong Ou, Palo Alto, CA (US); Zhiyong Li, Redwood City, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 354 days.

(21) Appl. No.: 12/771,753

(22) Filed: Apr. 30, 2010

(65) Prior Publication Data
US 2011/0267607 A1 Nov. 3, 2011

(51) Int. Cl.
G01J 3/40 (2006.01)
(52) U.S. Cl. ....................................... 356/301
(58) Field of Classification Search ................... 356/301
See application file for complete search history.

(56) References Cited

U.S. PATENT DOCUMENTS

| 7,224,451 | B2 | 5/2007 | Naya |
| 7,242,470 | B2* | 7/2007 | Cullum et al. ............... 356/301 |
| 7,288,419 | B2* | 10/2007 | Naya ........................... 438/20 |
| 7,351,588 | B2* | 4/2008 | Poponin ...................... 436/171 |
| 7,476,787 | B2 | 1/2009 | Thomas et al. |
| 7,576,854 | B2 | 8/2009 | Wang et al. |
| 7,586,601 | B2 | 9/2009 | Ebstein |
| 7,609,378 | B2* | 10/2009 | Konakahara ................. 356/301 |
| 7,651,863 | B2 | 1/2010 | Hulteen et al. |
| 7,656,525 | B2 | 2/2010 | Zhao et al. |
| 7,707,647 | B2* | 4/2010 | Konakahara ................... 850/32 |
| 2001/0006869 | A1 | 7/2001 | Okamoto et al. |
| 2004/0135997 | A1 | 7/2004 | Chan |
| 2006/0250613 | A1 | 11/2006 | Demuth |
| 2007/0015288 | A1 | 1/2007 | Hulteen et al. |
| 2007/0086001 | A1 | 4/2007 | Islam |
| 2008/0079104 | A1 | 4/2008 | Stewart et al. |
| 2009/0117646 | A1 | 5/2009 | Stordeur et al. |
| 2010/0062226 | A1 | 3/2010 | Hulteen et al. |
| 2010/0321684 | A1* | 12/2010 | Bratkovski et al. ........... 356/301 |
| 2011/0128536 | A1* | 6/2011 | Bond et al. ................... 356/301 |
| 2012/0013903 | A1* | 1/2012 | Kuo et al. ..................... 356/301 |
| 2012/0113419 | A1* | 5/2012 | Wang et al. .................. 356/301 |

FOREIGN PATENT DOCUMENTS

| WO | WO-2006/138442 A2 | 12/2006 |
| WO | WO-2009/117646 | 9/2009 |
| WO | WO-2010/056258 | 5/2010 |
| WO | WO-2011/014176 | 2/2011 |

OTHER PUBLICATIONS

Schmidt, et al., "Towards Easily Reproducible Nano-Structured SERS Substrates", *IEEE Sensors 2009 Conference*, (2009), pp. 1763-1767.

(Continued)

*Primary Examiner* — Layla Lauchman

(57) ABSTRACT

An integrated device for enhancing signals in Surface Enhanced Raman Spectroscopy (SERS). The integrated device comprising an array of nanostructures comprising a material, wherein the material is configured to allow light to pass through. The integrated device also comprising SERS active nanoparticles disposed on at least portion of the array of nanostructures and a mirror integrated below a base of the array of nanostructures. The mirror is configured to reflect light passing through the material into the array of nanostructures.

8 Claims, 4 Drawing Sheets

OTHER PUBLICATIONS

Wu, et al., "One-Kilobit Cross-Bar Molecular Memory Circuits at 30-nm Half-Pitch Fabricated by Nanoimprint Lithography", *Springer-Verlag, Pub online*, (Mar. 11, 2005), pp. 1173-1178.

Hu, et al., "Metal Coated Si Nanograss as Highly Sensitive SERS Sensors", *Proc. of SPIE*, vol. 7312, (2009), pp. 73120I-1-73120I-6.

Gilles, et al., "UV Nanoimprint Lithography with Rigid Polymer Molds", *Microelectronic Engineering 86*, (2009), pp. 661-664.

He, et al., "Large-Scale Synthesis of Flexible Free-Standing SERS Substrates with High Sensitivity: Electrospun PVA Nanofibers Embedded with Controlled Alignment of Silver Nanoparticles", *ACSNANO*, vol. 3, No. 12, (2009), pp. 3993-4002.

Application (PCT/US2008/083827), Nov. 2008.

Application (PCT/US2009/052308), Jul. 2009.

Cao, et al., "Enhance Raman Scattering from Individual Semiconductor Nanocones and Nanowires", Physical Review Letters PRL 96, 157402, Apr. 2006.

PCT Search Report, PCT/US2008/083827, May 2011.

PCT Search Report, PCT/US2009/052308, Jan. 20012.

* cited by examiner

ENHANCING SIGNALS IN SURFACE ENHANCED RAMAN SPECTROSCOPY (SERS)

CROSS-REFERENCE TO RELATED APPLICATIONS

This application is related to U.S. Patent Application 2011/0267606, published Nov. 3, 2011, filed on the same date as the present application and entitled "SURFACE-ENHANCED RAMAN SPECTROSCOPY DEVICE AND A MOLD FOR CREATING AND A METHOD FOR MAKING THE SAME", assigned to the assignee of the present application.

This application is related to U.S. Patent Application 2011/0267609, published Nov. 3, 2011, filed on the same date as the present application and entitled "APPARATUS FOR PERFORMING SERS", assigned to the assignee of the present application.

BACKGROUND

Raman spectroscopy is a spectroscopic technique used to study vibrational, rotational, and other low-frequency modes in molecular systems. In Raman spectroscopy, an approximately monochromatic beam of light of a particular wavelength range passes through a sample of molecules and a spectrum of scattered light is emitted. The spectrum of wavelengths emitted from the molecule is called a "Raman spectrum" and the emitted light is called "Raman scattered light." A Raman spectrum can reveal electronic, vibrational, and rotational energy levels of a molecule. Different molecules produce different Raman spectrums that can be used like a fingerprint to identify molecules and even determine the structure of the molecules.

The Raman scattered light generated by a compound (or ion) adsorbed on or within a few nanometers of a structured metal surface can be exponentially greater than the Raman scattered light generated by the same compound in a solution or in a gas phase. This process of analyzing a compound is called Surface Enhanced Raman Spectroscopy (SERS).

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
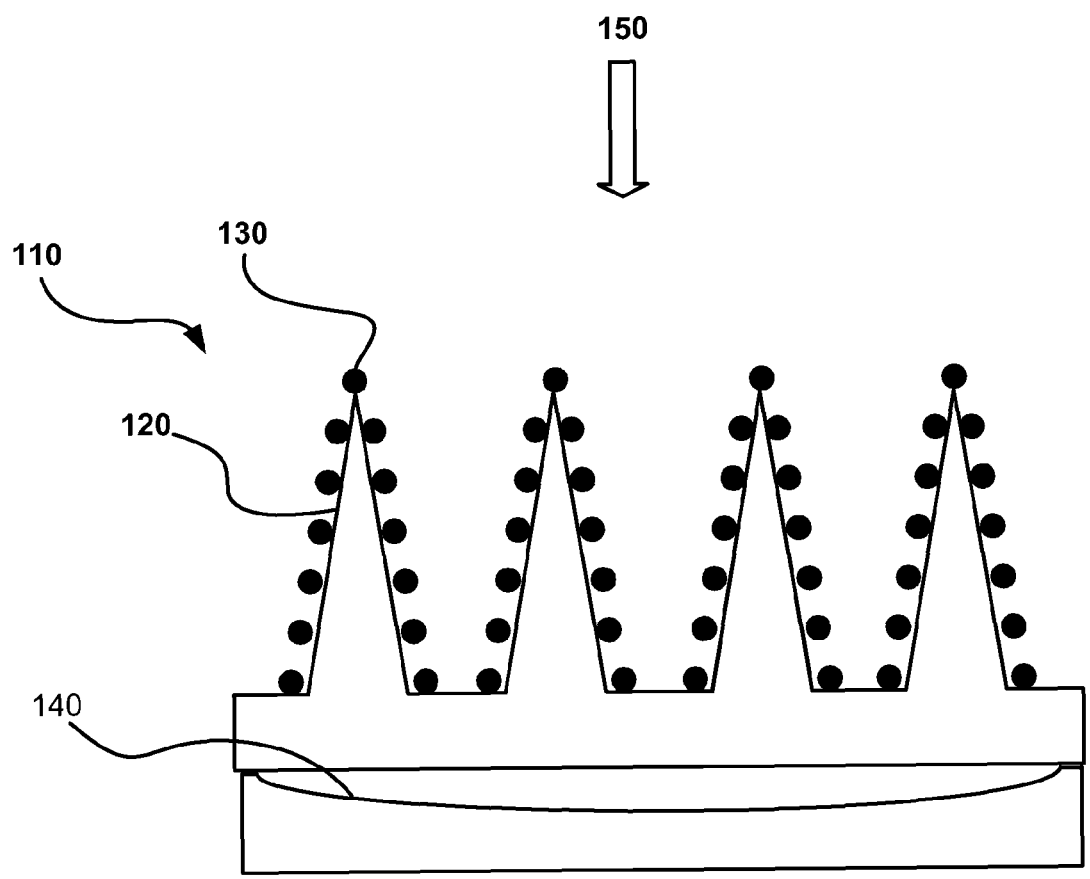
FIGS. 1-3 illustrate examples of an integrated device, in accordance with an embodiment of the present invention.

FIG. 1 depicts an integrated device 100 for enhancing signals in Surface Enhanced Raman Spectroscopy (SERS). Integrated device 100 includes an array of nanostructures 110, SERS active nanoparticles 130 and a mirror 140. Integrated device 100 optionally includes a resonant grating (e.g., resonant grating 250 of FIG. 2), which will be described in detail below.

In one embodiment, nanostructures 110 are three dimensional. For example, nanostructures 110 comprise a plurality of cones 120 or a plurality of substantially cone-shaped features (e.g., nanograss). In various embodiments, nanostructures 110 are any shape that is compatible with enhancing signals in SERS. In various examples, nanostructures 110 can be, but are not limited to, positive cone shapes, negative cone shapes, pillar shaped, hemisphere shaped, pyramid shaped and the like.

In another embodiment, nanostructures 110 can be either an aperiodic or a periodic array of nanostructures. For example, the periodic nanostructures 110 are regularly spaced along the x-direction (as shown in FIGS. 1-4) and regularly spaced in the z-direction (into the page). The height of nanostructures 110 (y-direction) can either be substantially equal or random. Moreover, the height and base dimensions can be selected to support guided-mode resonance for various light 150 wavelengths.

Nanostructures 110 are configured to allow light 150 to pass through. In various embodiments, nanostructures 110 are comprised of a translucent or transparent material. For example, nanostructures 110 are comprised of glass or polymer. The transparent or translucent property of the material of nanostructures 110 enhances signals in SERS, which will be described in detail below.

SERS active nanoparticles 130 are disposed on at least a portion of nanostructures 110. In one embodiment, SERS active nanoparticles 130 are deposited (e.g., electron beam deposition) metal particles. For example, SERS active nanoparticles 130 can be, but are not limited to, silver, gold, platinum and copper.

FIGS. 1-4 depict SERS active nanoparticles 130 evenly dispersed on the outer surface of nanostructures 110. However, in various embodiments, SERS active nanoparticles 130 can be randomly dispersed on the outer surface of nanostructures 110. Also, SERS active nanoparticles 130 cover the entire outer surface of nanostructures 110.

Figure 2:
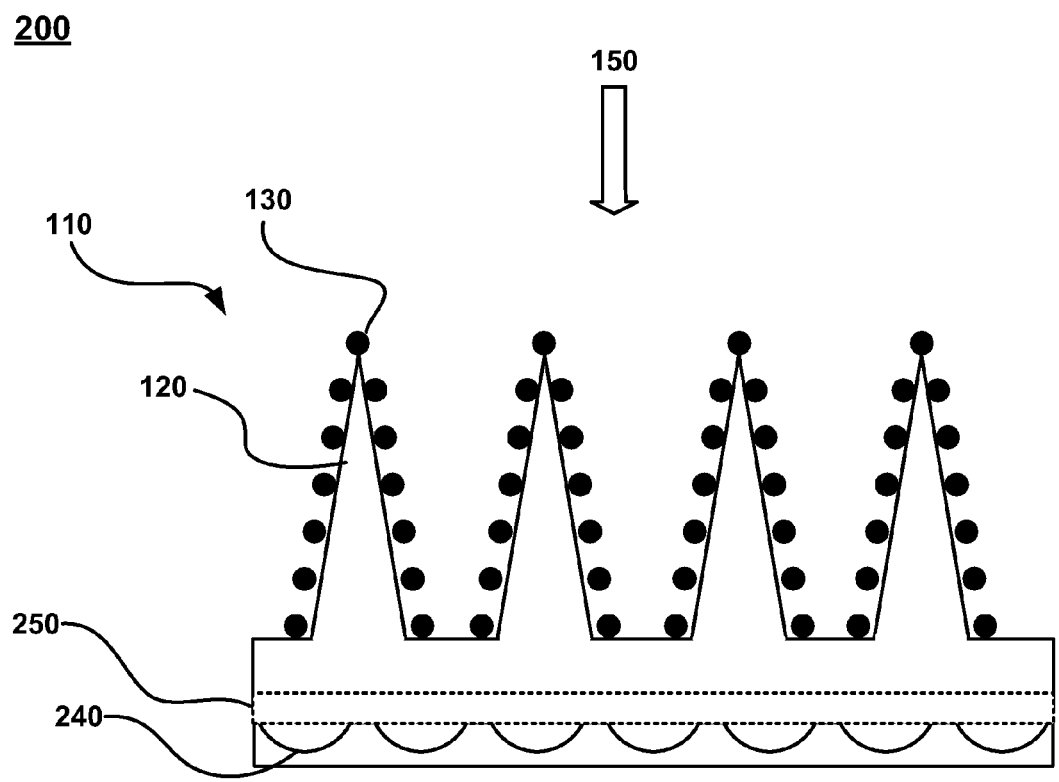

Mirror 140 is integrated below a base of nanostructures 110. Mirror 140 is configured to reflect light that passes through the material of the nanostructures 110 back into nanostructures 110. In one embodiment, mirror 140 is a single concave mirror disposed and integrated below a base of nanostructures 110. In another embodiment, as depicted in FIG. 2, a plurality of concave mirrors 240 are integrated below a base of nanostructures 110.

During use, light 150 (e.g., Raman-excitation light) is emitted towards integrated device 100 to facilitate in detecting analyte molecules (not shown) located on, or in close proximity to, SERS active nanoparticles 130. As light 150 is incident upon the analyte molecules, a Raman-scattered light is reflected off of the analyte molecules. Additionally, the combination of SERS active nanoparticles 130 and nanostructures 110 cause enhancement of the intensity of the Raman-scattered light from the analyte molecules.

Moreover, as light 150 passes through nanostructures 110, light 150 reflects off of mirror 140 and back into and subsequently out of nanostructures 110. As a result, nanoparticles 130 and analyte molecules are excited once again (e.g., double excitation). Thus, the intensity of the Raman-scattered light from the analyte molecules is enhanced even further.

In particular, the wavelengths selected for light 150 cause analyte molecules to emit a Raman spectrum of Raman scattered light over a range of wavelengths. The intensity of the Raman scattered light may also be enhanced as a result of two mechanisms associated with the SERS active nanoparticles 130 (e.g., Raman active material). The first mechanism is enhanced electromagnetic field produced at the surface of the SERS active nanoparticles 130 resulting from the collective oscillation of the conduction band electrons, or so called "localized surface Plasmon resonance". The second mechanism could be the cone mediated surface Plasmon focusing effect leading to an enhanced electromagnetic field at the tip of the cone structure.

Analyte molecules adsorbed on or in close proximity to the SERS active nanoparticles 130 experience a relatively strong electromagnetic field. Molecular vibrational modes directed normal to the SERS active nanoparticles 130 are most strongly enhanced. The intensity of the surface Plasmon polariton resonance depends on many factors including the wavelengths of light 150. The second mode of enhancement, charge transfer, may occur as a result of the formation of a charge-transfer complex between the surfaces of the SERS active nanoparticles 130 and the analyte molecules. The electronic transitions of many charge transfer complexes are typically in the visible range of the electromagnetic spectrum.

Still referring to FIG. 1, in various embodiments, mirror 140 increases the effective numeric aperture. For example, the higher order of numeric aperture, the increased ability to collect a higher cone angle of emitted Raman light. i.e., mirror 140 can help collect certain angle distribution of Raman scattered light and focus it into a narrower distribution angle.

FIG. 2 depicts an integrated device 200, in accordance to an embodiment of the present invention. Integrated device 200 is similar to integrated device 100 and includes an array of nanostructures 110 and SERS active nanoparticles 130. However, integrated device 200 includes a plurality of concave mirrors 240. Integrated device 200 optionally includes a resonant grating 250.

Concave mirrors 240 function similarly as concave mirror 140, as described above. In particular, concave mirrors 240 are integrated below a base of nanostructures 110. Concave mirrors 240 are configured to reflect light that passes through the material of the nanostructures 110 back into nanostructures 110.

Resonant grating 250 is integrated below a base of nanostructures 110. Resonant grating 250 is configured to establish a guided-mode resonance with light passing through integrated device 200. Resonant grating 250 can be, but is not limited to, a dielectric grating or a metal grating.

Resonant grating 250 supports guided-mode resonance with certain wavelengths of light 150. Guided-mode resonance enhances, or increases, the intensity of the associated electro magnetic field. As a result, Raman-excitation light can be emitted or coupled out through nanostructures 110. The enhanced electromagnetic field also interacts with the Raman-active material to further enhance this emission process for analyte molecules located on, or in close proximity to, SERS active nanoparticles 130.

Figure 3:
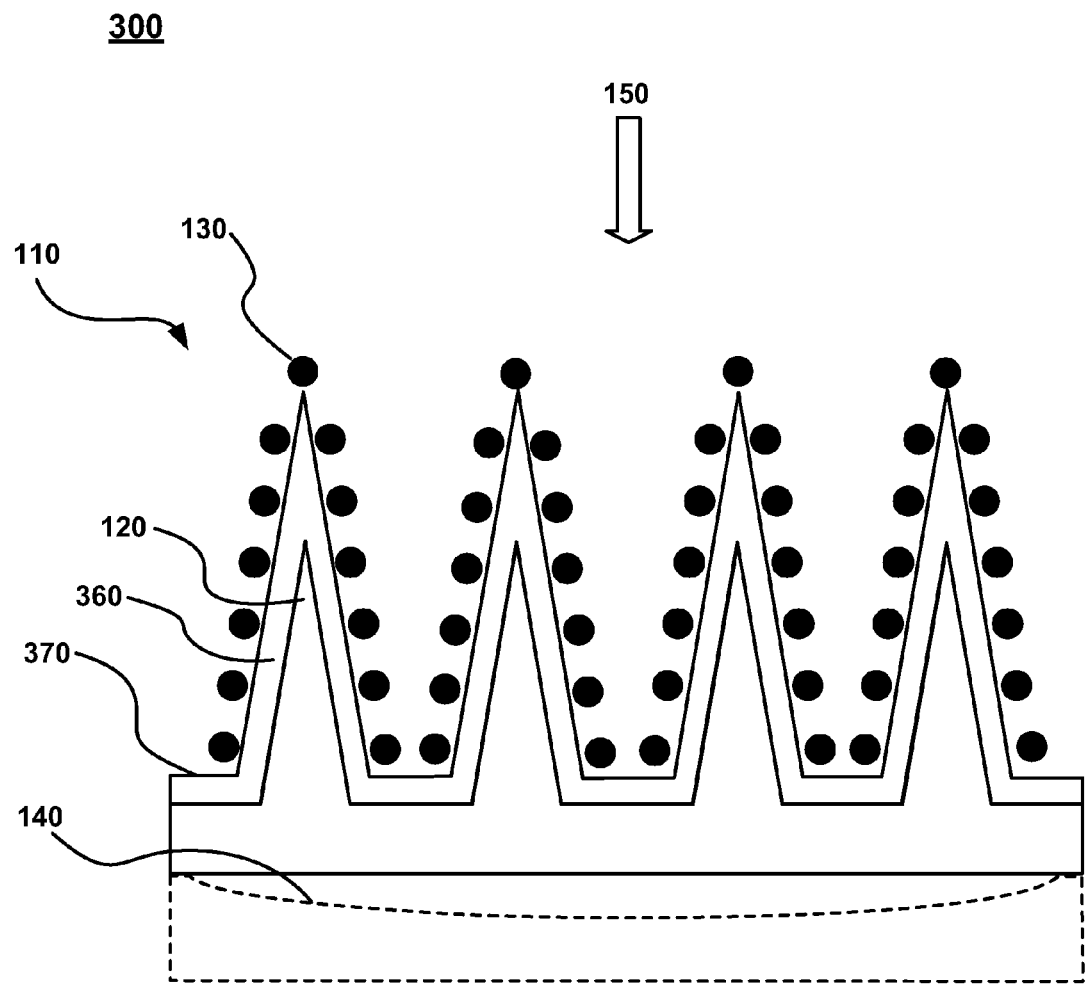

FIG. 3 depicts an integrated device 300, in accordance to an embodiment of the present invention. Similar to FIGS. 1 and 2, integrated device 300 includes an array of nanostructures 110 and SERS active nanoparticles 130. However, integrated device 300 also includes a thin metal layer 360 and a thin dielectric layer 370. Integrated device 300 optionally includes any combination of resonance grating 250, concave mirror 140 and/or a plurality of concave mirrors 240, as described above.

Metal layer 360 is disposed on a surface of nanostructures 110. Metal layer 360 is configured to reflect light 150 and also allow light 150 to pass through. In various embodiments, metal layer 360 has a thickness in the range of about 5 nanometers (nm) to 200 nm. Also, metal layer 360 can be, but is not limited to, at least one metal selected from silver, gold and copper.

Metal layer 360 is transparent or translucent. Propagating Surface Plasmon polariton of metal layer 360 can be excited due to light 150. Therefore, metal layer 360 can create a strong excitation signal.

Dielectric layer 370 is disposed on a surface of metal layer 360. Dielectric layer 370 is configured to allow light 150 to pass through. Dielectric layer 370 has a thickness that allows analyte molecules to be subject to any plasmonic field on metal layer 360. In one embodiment, dielectric layer 370 is a material (e.g., analyte molecules).

Figure 4:
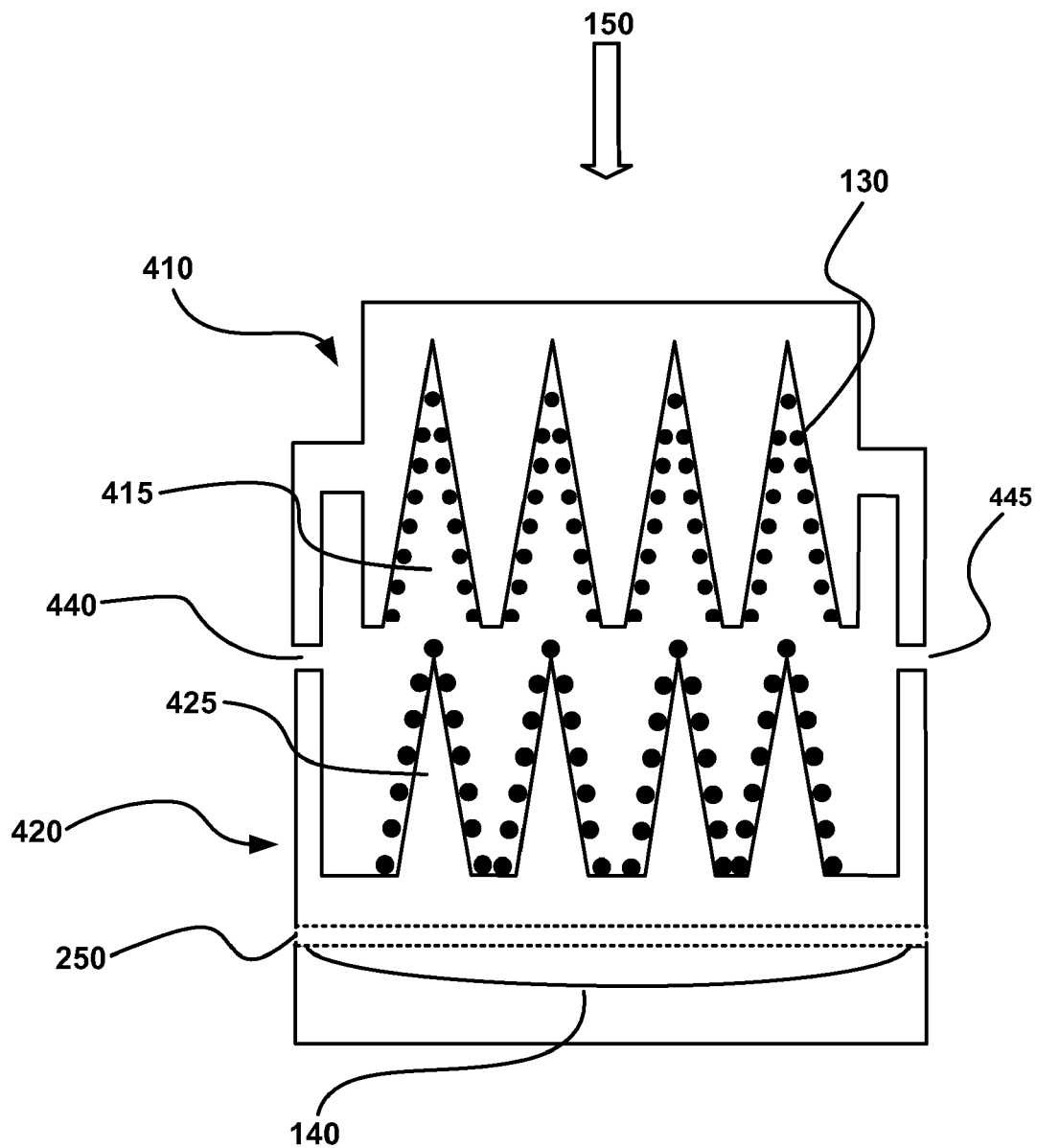
FIG. 4 illustrates an enclosure, in accordance with an embodiment of the present invention.

FIG. 4 depicts an enclosure 400 for enhancing signals in SERS, in accordance to an embodiment of the present invention. Enclosure 400 includes first array of nanostructures 410, second array of nanostructures 420, mirror 140, SERS active nanoparticles 130, inlet 440 and outlet 445. Enclosure 400 optionally includes resonance grating 250, as described above.

First array of nanostructures 410 includes a plurality of negative cones 415. In contrast, second array of nanostructures 420 includes a plurality of positive cones 425. In various embodiments, first and second array of nanostructures can include any combination of positive nanostructures (e.g., cones) or negative nanostructures. For example, first array of nanostructures 410 are negative cones and second array of nanostructures 420 are negative cones.

First and second array of nanostructures 410 and 420 are configured to allow light 150 to pass through. In various embodiments, first and second array of nanostructures 410 and 420 are comprised of a translucent or transparent material. For example, first and second array of nanostructures 410 and 420 are comprised of glass or polymer. It should be appreciated that first and second array of nanostructures enhance signals related to SERS, as described above.

In one embodiment, first array of nanostructures 410 face second array of nanostructures 420. In another embodiment, first array of nanostructures 410 are aligned with second array of nanostructures 420. For example, a peak of cone 425 is aligned with a negative peak of negative cone 415.

Mirror 140 is integrated below a base of second array of nanostructures 420. Mirror is configured to reflect light 150 that passes through both first and second array of nanostructures 410 and 420 back into first and second array of nanostructures 410 and 420. In various embodiments, mirror 140 is a single concave mirror or a plurality of concave mirrors (e.g., mirrors 240 of FIG. 2).

In various embodiments, the mirror(s) can be, but are not limited to, convex mirror(s), cylindrical mirror(s) and any combination thereof.

During use, light 150 (e.g., Raman-excitation light) is emitted towards integrated device 100 to facilitate in detecting analyte molecules (not shown) located on, or in close proximity to, SERS active nanoparticles 130. The analyte molecules are provided through inlet 440 and exit at outlet 445. In one embodiment, analyte molecules are introduced into enclosure 400 via gas flow through inlet 440 and outlet 445.

As light 150 is incident upon the analyte molecules, a Raman-scattered light is reflected off of the analyte molecules. Additionally, the combination of SERS active nanoparticles 130 and first and second array of nanostructures 410 and 420 cause enhancement of the intensity of the Raman-scattered light from the analyte molecules.

Moreover, as light 150 passes through first and second array of nanostructures 410 and 420, light 150 reflects off of mirror 140 and back into and subsequently out of first and second array of nanostructures 410 and 420. As a result, SERS active nanoparticles 130 and analyte molecules are excited once again (e.g., double excitation). Thus, the intensity of the Raman-scattered light from the analyte molecules is enhanced even further.

In one embodiment, inlet 440 and outlet 445 are closed after analyte molecules are introduced in enclosure 440. As a result, Raman-scattered light from the analyte molecules is enhanced even further.

In various embodiments, a plurality of enclosures 400 are stacked up with one another. It should also be appreciated that any combination of array of nanostructures and/or any combination of enclosures (e.g., enclosure 400) can be combined to facilitate in enhancing signals in SERS.

In various embodiments, array of nanostructures (e.g., positive array of nanostructures and/or negative array of nanostructures) can be created by black silicon (black Si) that includes an array of nanostructures. In such embodiments, black Si can be used as a mold. The array of nanostructures on the black Si is imprinted onto a first substrate, such as glass or polymer. As a result, a negative array of nanostructures are created on the first substrate. The first substrate can be utilized as a mold and/or an array of negative nanostructures for use in SERS.

When used as a mold, a positive array of nanostructures can be imprinted on a second substrate, such as glass or polymer. As a result, the array of positive nanostructure on the second substrate can be utilized as an array of positive nanostructures for use in SERS. It should be appreciated that the array of nanostructures can be large area (e.g., larger than a 6 inch wafer).

The process of creating array of nanostructures can be, but is not limited to, nanoimprint lithography (NIL).

Various embodiments of the present invention are thus described. While the present invention has been described in particular embodiments, it should be appreciated that the present invention should not be construed as limited by such embodiments, but rather construed according to the following claims.

The invention claimed is:

1. An integrated device for enhancing signals in Surface Enhanced Raman Spectroscopy (SERS), said device comprising:
    an array of nanostructures comprising a material, wherein said material is configured to allow light to pass through;
    a metal layer disposed on a surface of said array of nanostructures, wherein said metal layer is configured to reflect incident light and allow light to pass through;
    a dielectric layer disposed on a surface of said metal layer, wherein said dielectric layer is configured to allow light to pass through; and
    SERS active nanoparticles disposed on at least portion of said dielectric layer.

2. The integrated device of claim 1, comprising:
    a mirror integrated below a base of said array of nanostructures, wherein said mirror is configured to reflect light passing through said material into said array of nanostructures.

3. The integrated device of claim 2, wherein said mirror is selected from a group consisting of:
    a single concave mirror and a plurality of concave mirrors.

4. The integrated device of claim 1, wherein said array of nanostructures comprise:
    a periodic array of nanostructures.

5. An enclosure for enhancing signals in Surface Enhanced Raman Spectroscopy (SERS), said device comprising:
    a first array of nanostructures comprising a material, wherein said material is configured to allow light to pass through;
    a second array of nanostructures comprising said material, wherein said first array of nanostructures face said second array of nanostructures;
    SERS active nanoparticles disposed on at least portion of said first array of nanostructures and said second array of nanostructures; and
    a mirror integrated below a base of said second array of nanostructures, wherein said mirror is configured to reflect light passing through said material into said second array of nanostructures and said first array of nanostructures.

6. The enclosure of claim 5, wherein said mirror is selected from a group consisting of:
    a single concave mirror and a plurality of concave mirrors.

7. The enclosure of claim 5, wherein said first array of nanostructures and
    said second array of nanostructures are selected from a group consisting of:
        positive cones and negative cones.

8. The enclosure of claim 5, further comprising:
    a resonant grating integrated below a base of said second array of nanostructures, wherein said resonant grating is configured to establish a guided-mode resonance with light passing through said material.

* * * * *